US008822643B2

(12) United States Patent
Rossi et al.

(10) Patent No.: US 8,822,643 B2
(45) Date of Patent: Sep. 2, 2014

(54) PROCESS FOR THE PREPARATION OF A VIRUS-INACTIVATED FV CONCENTRATE STARTING FROM HUMAN PLASMA, SCALABLE TO INDUSTRIAL LEVEL

(75) Inventors: Paola Rossi, Castiglione di Gafagnana (IT); Ilaria Nardini, Barga (IT); Pierangelo Giovacchini, Lammari-Capannori (IT); Filippo Mori, Lucca (IT); Claudio Farina, Pisa (IT)

(73) Assignee: Kedrion S.p.A., Castel Vecchio Pascoli (IT)

( * ) Notice: Subject to any disclaimer, the term of this patent is extended or adjusted under 35 U.S.C. 154(b) by 0 days.

(21) Appl. No.: 14/112,264

(22) PCT Filed: Apr. 20, 2012

(86) PCT No.: PCT/EP2012/057262
§ 371 (c)(1),
(2), (4) Date: Oct. 17, 2013

(87) PCT Pub. No.: WO2012/143507
PCT Pub. Date: Oct. 26, 2012

(65) Prior Publication Data
US 2014/0039160 A1      Feb. 6, 2014

(30) Foreign Application Priority Data
Apr. 22, 2011   (IT) ................ FI2011A0084

(51) Int. Cl.
| | | |
|---|---|---|
| A61K 38/00 | (2006.01) | |
| C07K 14/745 | (2006.01) | |
| C07K 14/75 | (2006.01) | |
| C07K 1/22 | (2006.01) | |
| C07K 1/36 | (2006.01) | |
| C07K 1/18 | (2006.01) | |
| G01N 30/02 | (2006.01) | |
| C07K 1/16 | (2006.01) | |

(52) U.S. Cl.
CPC .............. *C07K 1/16* (2013.01); *C07K 14/745* (2013.01)
USPC .......... 530/381; 530/390.1; 530/412; 530/416

(58) Field of Classification Search
None
See application file for complete search history.

(56) References Cited

FOREIGN PATENT DOCUMENTS

| | | |
|---|---|---|
| EP | 0244834 B1 | 3/1992 |
| JP | 56049394 | 5/1981 |
| WO | 9401466 | 1/1994 |
| WO | 9529259 | 11/1995 |
| WO | 2010069946 A1 | 6/2010 |

OTHER PUBLICATIONS

Clifton et al. "Use of prteomics for validation of the isolation process of clotting factor IX from human plasma" Journal of Proteomics 2010 73 678-688.*
Kane et al. "Purification and characterization of human coagulation factor V" Journal of Biological Chemistry 1981 256 1002-1007.*
Horowitz et al. "Solvent detergent treated plasma:a virus inactivated substitute for fresh frozen plasma" Blood 1992 79 826-831.*
Burnouf et al. "Nanofiltration of plasma-derived biopharmaceutical products" Haemophilia 2003 9, 24-37.*
Tran-Thang et al. "Tissue-type plasminogen activator increases the binding of Glu-plasminogen to clots" J. Clin. Invest. 1984 74 2009-2016.*
Esmon C.T.; "The Subunit Structure of Thrombin-Activated Factor V Isolation of Activated Factor V, Separation of Subunits, and Reconstitution of Biological Activity"; Journal of Biological Chemistry, American Society of Biological Chemists, vol. 254, No. 3, 1979, pp. 964-973.
Liu et al.; "Isolation and Purification of Human Coagulation Factor V"; Vox Sanguinis, 20th Regional Congress of the International Society for Blood Transfusion; vol. 97; 2009; p. 104.
Dahlback B.; "Human coagluation factor V purification and thrombin-catalyzed activation"; The Journal of Clinical Investigation Sep.; vol. 66; 1980; pp. 583-591.
Chulkova et al.; "The preparation and properties of factor V from bovine plasma"; Clinica Chimica Acta, vol. 62; 1975; pp. 21-28.
International Search Report for PCT/EP2012/057262 Dated June 21, 2012.

* cited by examiner

*Primary Examiner* — Suzanne M Noakes
*Assistant Examiner* — Gerard Lacourciere
(74) *Attorney, Agent, or Firm* — Abelman, Frayne & Schwab

(57) ABSTRACT

The present invention provides a process for purifying FV starting from human plasma or a fractionation intermediate thereof, that is simple, scalable to the industrial level and relatively inexpensive compared to the methods described in the literature to date. The invention consists of the use of two anion exchange chromatography steps, the first of which has the purpose of separating the FV from the PTC component factors, while the second has the purpose of isolating the protein of interest from the majority of plasma proteins by means of selective interaction with the weak anion exchange support used. The process developed has also had a viral inactivation step and a viral removal step included, contributing to the safety of the final product obtained, without however significantly altering the process total recovery of FV, and without necessitating the introduction of additional steps for eliminating the inactivating agents used, thanks to the order in which the various steps are conducted. The process described in the present invention also enables an FV concentrate to be obtained that is stable once frozen at −20° C.

7 Claims, 3 Drawing Sheets

PROCESS FOR THE PREPARATION OF A VIRUS-INACTIVATED FV CONCENTRATE STARTING FROM HUMAN PLASMA, SCALABLE TO INDUSTRIAL LEVEL

CROSS-REFERENCE TO RELATED APPLICATIONS

This application is a National Phase of PCT/EP2012/057262, filed 20 Apr. 2012 which claims the priority of Italian Application No. FI2011A000084, filed 22 Apr. 2011, all of which are incorporated herein by reference.

FIELD OF THE INVENTION

The present invention relates to the field of blood products, in particular the purification of human FV. In particular it relates to obtaining an FV concentrate suitable for the treatment of pathologies associated with deficiencies/changes in this protein.

STATE OF THE ART

Factor V plays an essential role in the blood coagulation cascade. Following its activation by thrombin and FXa, it acts as a co-factor of FXa itself in the prothrombinase complex, resulting in a significant increase in the rate of thrombin generation. The activity of FVa is then down-regulated by hydrolysis by APC. Besides this pro-coagulant function, FV also acts as an anti-coagulant: hydrolysis of the single chain of FV by APC converts FV into a molecule that acts as a cofactor of APC itself in the inactivation of FVIIIa.

Approx. 80% of the FV circulates in plasma at a concentration of 7-10 µg/ml; the remaining 20% is accumulated in platelet α-granules. Plasma FV is synthesised by hepatocytes as a single-chain pro-cofactor with an MW of 330 KDa; the platelet fraction, partially proteolysed and associated with multimerin, is partly synthesised in megakaryocytes and partly absorbed from plasma by endocytosis. Structurally, the single FV chain is organised into structural domains A1-A2-B-C1-C2; proteolytic removal of domain B generates FVa, which is composed of two chains held together by non-covalent bonds and stabilised by $Ca^{++}$ ions. In particular, hydrolysis by FXa and thrombin at aminoacid residues Arg709, Arg1018 and Arg1545, results in the release of FVa consisting of a heavy chain, with MW of 105 KDa, and a light chain with MW of 74-71 KDa. Down-regulation of FVa by APC is then achieved by means of proteolysis at residues Arg506, Arg306 and Arg679; an alternative thrombin-mediated mechanism of FV inactivation is achieved by hydrolysis at Arg643 in the presence of endothelial cells. Hydrolysis of the single FV chain by APC at Arg506 converts FV into a molecule with anticoagulant activity.

APC-resistant forms of FV are described in the literature, such as FV-Leiden, FV-Cambridge and FV-Hong Kong, resulting in prolongation of FVa activity, associated with the occurrence of thrombotic phenomena. Another form of coagulation disorder, attributable to FV deficiency, and thus characterised by haemorrhagic episodes, is also known. More precisely, Parahaemophilia, an extremely rare pathology with an incidence of 1 case in 1,000,000, classifiable among the Recessively Inherited Coagulation Disorders (RICD), is recognised as a qualitative (Type II) or quantitative (Type I) congenital defect of FV, transmitted in an autosomal recessive manner. Acquired FV deficiency is also possible as a consequence of the development of inhibitors, generally arising from the topical use of bovine thrombin, rheumatic pathologies or antibiotic treatments. Since a portion of circulating FV is contained inside platelet α-granules, a reduction in its concentration can also occur in the case of changes to the latter. Clinical manifestations of FV deficiency, attributable to the pro-coagulant function of this protein, vary in extent and frequency, and are mainly represented by cutaneous and mucocutaneous bleeding, but also muscular haemorrhaging, haemarthrosis, genitourinary, gastrointestinal and CNS bleeding episodes. Another related pathology is the congenital deficiency associated with Factor V and Factor VIII, itself also a very rare haemorrhagic disease, wherein there is a concomitant reduction in the concentration of both factors, generally of between 5% and 20% of normal plasma levels. In this case, the main cause of the pathology is represented by a defect in a single gene causing altered transport of the two hepatic cell factors in the blood stream. The haemorrhagic symptomatology is similar to that observed with FV deficiency, but with increased frequency of haemarthrosis (50% of cases).

The rarity of the pathologies associated with FV deficiency is reflected in the slow therapeutic progress. Indeed, replacement therapy for patients affected by parahaemophilia and combined Factor V and Factor VIII deficiency can currently only be based on the use of Fresh Frozen Plasma (FFP). However, the use of FFP does not represent an ideal treatment, particularly due to the resulting side effects, principally increased plasma volume, requiring careful monitoring and the possible administration of diuretics, and the risk of viral infection.

Possible alternatives include the use of antifibrinolytic agents, which are only effective in the treatment of minor haemorrhages, or the administration of rFVlla and FEIBA, which do not however constitute a specific treatment, and can sometimes give rise to a risk of thrombosis.

The availability of an FV concentrate, with a good level of purity and safe from a viral viewpoint, might thus offer a more effective and targeted therapeutic alternative in the treatment of FV deficiencies.

Due to the lack of interest in the development of purified FV-containing products, there are currently no purification processes consisting of a limited number of steps making it possible to obtain good yields of FV suitable for the production of said protein on an industrial scale.

In traditional plasma fractionation, there are no steps where there is enrichment of FV, whereby numerous purification processes have been developed which in the majority of cases make it possible to obtain FV from plasma or cryo-depleted supernatant. The FV purification methods described in the literature almost always foresee the use of numerous steps, many of which consisting of precipitation steps with excipients that are often difficult to remove from the end product, and/or the use of expensive chromatographic methods that are not easily available, such as those involving immunoaffinity.

The first attempts at FV purification described in the literature envisage the use of classic aluminium hydroxide and barium chloride precipitation methods. Almost all studies envisage the use of PEG, frequently in combination with other precipitation steps. Said precipitations, which can cause the denaturation and inactivation of labile proteins such as FV, have been predominantly used with the aim of separating FV from prothrombin complex proteins such as FII, FVII, FIX and FX. Precipitation with aluminium hydroxide is also described in some patents: in JP56049394(A), fraction II derived from Cohn fractionation, is incubated with a monosaccharide and then precipitated using said oxide, so as to separate the FV from the coagulation factors which might trigger the coagulation cascade. Patent CA1293214(C)-1991 also describes a process for the purification of FV starting from human plasma or cryo-depleted supernatant, involving precipitation with aluminium hydroxide as a first step, followed by incubation with DEAE Sephadex A50 resin and subsequent ammonium sulphate precipitation.

Indeed alternatively, or in association with precipitation techniques, chromatography purification steps have been used with various techniques, including: hydroxyapatite absorption interaction, gel permeation, affinity, hydrophobic interaction, immunoaffinity.

The chromatographic purification step most frequently included however is ion exchange, in particular anion exchange, using supports bonded to weak or strong cationic functional groups.

Among the strong anion exchangers are reported supports with quaternary ammonium groups on cellulose or agarose matrices. The weak anion exchangers predominantly used have DEAE functional groups on cellulose, agarose or dextran matrices.

In the processes reported in the patents describing the purification of FV, the support DEAE Sephadex A50 is frequently used as an anion exchanger in binding mode.

In the U.S. Pat. No. 5,219,995, the first purification step involves incubation of the plasma or cryo-depleted supernatant with said chromatography medium with 0.03 M phosphate buffer and 0.03 M citrate, and subsequent elution of the FV together with factors II, IX and X with 0.03 M phosphate buffer and 0.03 M citrate, containing 0.2 M sodium chloride. In order to separate the FV from the aforementioned factors, a subsequent barium chloride precipitation step is performed. The FV recovered in the supernatant is thus partially purified, even if the resulting specific activity, evaluated by spectrophotometric assay, is very low (S.A. FV: 0.027 IU/mg).

On the other hand, patent EP0756638B1 describes an initial screening of plasma fractionation intermediates in order to verify the most suitable fraction to be used as starting material for the purification and, after having verified the recovery of at least 80% of the FV in the cryo-depleted supernatant, investigates the binding of the protein to DEAE Sephadex, in the step used in the traditional fractionation process for the purification of PTC. Indeed, it is demonstrated that by increasing the resin/sample ratio with respect to the standard process and altering the ionic strength of the supernatant, it is possible to increase the yield of FV in the eluate containing the crude PTC. In any case, the optimisation described for the resin binding step foresees elution of the FV together with the prothrombin complex and the attainment of a very impure product (S.A. FV: 0.4 IU/mg).

In patent CA1293214(C)-1991, FV is once more purified starting from plasma or cryo-depleted supernatant, and in the first step, the prothrombin complex component factors are precipitated using aluminium hydroxide, while the FV is recovered in the supernatant. The FV-containing fraction is then incubated in batch with the DEAE Sephadex A50 resin in a very high ratio (13.6 g/L of sample) at pH 7.5 in 0.02 M citrate buffer and 0.06 M NaCl, thus obtaining the binding of the FV to the support, which is subsequently transferred to a chromatography column. The FV-containing eluate is thus obtained by washing with a solution containing 1 M NaCl, 1 IU/ml heparin, 0.2 IU/ml ATIII and 5 mM $CaCl_2$. Furthermore, to obtain a stable preparation of FV, the presence of anticoagulants is unsuitable, and must later be removed from the product, but the eluate undergoes further precipitation with ammonium sulphate, followed by resuspension, dialysis and freeze-drying. In addition, yield, specific activity or stability data are not available for the product obtained by means of this laborious and aggressive process.

Therefore, the FV-purification methods described to now envisage the use of numerous purification steps, including precipitation methods that can cause denaturation and inactivation of the FV. Separation of the FV from the prothrombin complex factors, necessary for obtaining a product containing stable FV, has indeed only been obtained by using this type of aggressive technique or by using antibodies directed against FV, which, with the involvement of expense and the not insignificant difficulty in execution, have been attached to chromatography supports and used to isolate the FV. Even the more recently described processes, envisaging milder treatment of the protein and its isolation by immunoaffinity and anion exchange alone (WO 2010/069946), do not allow satisfactory yields of FV (no greater than 30%) and involve all the difficulties associated with use of an immunoaffinity support. This includes complicated preparation of the chromatography medium and a low number of reuse cycles: indeed, the functional groups presenting the antibody have greater susceptibility to aggressive treatments such as regeneration and exposure to extreme pH with respect to classic functional groups.

In the few processes described where the stability of the FV in the end product has been evaluated, the protein only maintains its integrity through the addition of a protease inhibitor cocktail (including Benzamidine, DFP, PMSF and STI) in all of the steps, which must then be removed prior to final formulation of the product.

With regard to the viral safety of the product, which must be guaranteed for clinical use, the only process described containing a single viral inactivation step uses heptane for this purpose (U.S. Pat. No. 5,219,995): The freeze-dried intermediate is resuspended in n-heptane and heated at 60° C. for 20 h, then the inactivating agent is removed by drying the product. Besides being insufficient in anticipation of clinical use, the viral inactivation treatment described in said patent is potentially damaging to the integrity of the protein of interest.

It is thus evident that there is currently no process for the purification of FV that is simple, rapid and easily scalable for industrial production that makes it possible to obtain an intact protein with good yield.

The scope of the present invention is therefore to provide a simple method, applicable on an industrial scale, that makes it possible to obtain a virus inactivated FV concentrate, purified with high yield, wherein the integrity of the protein is preserved as much as possible, guaranteeing the viral safety of the product and that is suitable for clinical use by parenteral administration.

| DEFINITIONS AND ABBREVIATIONS | |
|---|---|
| FV: | factor V |
| FVa: | activated factor V |
| FXa: | activated factor X |
| APC: | activated protein C |
| RICD: | recessively inherited coagulation disorder |
| CNS: | central nervous system |
| FFP: | fresh frozen plasma |
| rFVIIa: | recombinant activated factor VII |
| FEIBA: | activated prothrombin complex |
| FVII: | factor VII |
| FII: | factor II |
| FIX: | factor IX |
| FX: | factor X |
| PTC: | prothrombin complex |
| TnBP: | tri-n-butyl phosphate |
| DEAE: | diethylaminoethyl |
| DFP: | diisopropyl fluorophosphate |
| PMSF: | phenylmethanesulphonyl fluoride |
| STI: | soybean trypsin inhibitor |
| WFI: | water for injectables |

SUMMARY OF THE INVENTION

The present invention describes a process for the purification of FV starting from human plasma, or an intermediate fraction enriched in FV, wherein the protein is intact, preferably cryosupernatant. Said process comprises two chromatography steps on weak anion exchangers, preferably having DEAE functional groups, wherein the first step is conducted in FV "non-binding" mode while the second is in FV "capture" mode.

The process according to the invention is easily scalable to the industrial level and makes it possible to obtain an FV concentrate with high yield, that is virally safe and has a level of purification suitable for use in the treatment of pathologies associated with FV deficiency, in particular Parahaemophilia and FV and FVIII associated deficiencies, pathologies that currently have no effective treatment.

The first purification step has been devised in order to separate the FV from the other coagulation factors, particularly FVII, FII, FIX and FX, a step that is fundamental for guaranteeing greater integrity of the protein of interest. Said step consists of a batch incubation of the resin and cryosupernatant under such pH, conductivity and charge conditions as to allow binding of the contaminating factors to the resin and recovery of the FV in the non-absorbed fraction; said fraction is thus obtained by means of a simple filtration method making it possible to separate the resin from the plasma filtrate. The intermediate thus produced is subjected to a second chromatography step envisaging: binding of the FV to the anion exchanger, removal of the contaminating proteins by means of wash buffers, elution of the FV by increasing the ionic strength in the elution buffer.

The present method of the invention has the following advantages with respect to what has been described in the aforementioned patents and publications:

It is a simple and easily executable method, in that by means of just two chromatography steps, it make is possible to obtain a purified FV concentrate with good yield.

Unlike what has been reported in the literature, the FV is separated from the prothrombin complex factors by means of a mild and low-cost purification step. Indeed, the step in question consists of batch incubation of the cryo-depleted supernatant, preferably with DEAE Sephadex A50 resin, wherein the conductivity of the cryo-depleted supernatant and the resin/sample volume ratio have been appropriately adjusted, so as to identify conditions where the FV is not bound and at the same time FII, FVII, FIX and FX are bound. On the other hand, the published or patented works envisage obtaining said result by means of precipitation techniques, thus somewhat drastic and potentially inactivating a good part of the FV present, or by means of immunoaffinity techniques, implying numerous difficulties in the preparation of the chromatography support and being much more costly compared to that what is reported in the present invention.

The separation of FV from the PTC component proteins, a condition essential for maintaining the integrity of the protein, occurs during the first step of the purification process; operating in this manner prevents the co-purification of FV together with the aforementioned PTC factors due to absorption onto the DEAE Sephadex A50 support, which would result in its activation and hence its consequent inactivation, as shown in example 1.

The present method also makes it possible to be able to use the resin-absorbed fraction complex for the standard purification of PTC, possibly even containing 4 components, given that not only FII, FIX and FX bind to the support, but FVII is also almost completely absorbed onto it.

DETAILED DESCRIPTION OF THE INVENTION

Figure 1:
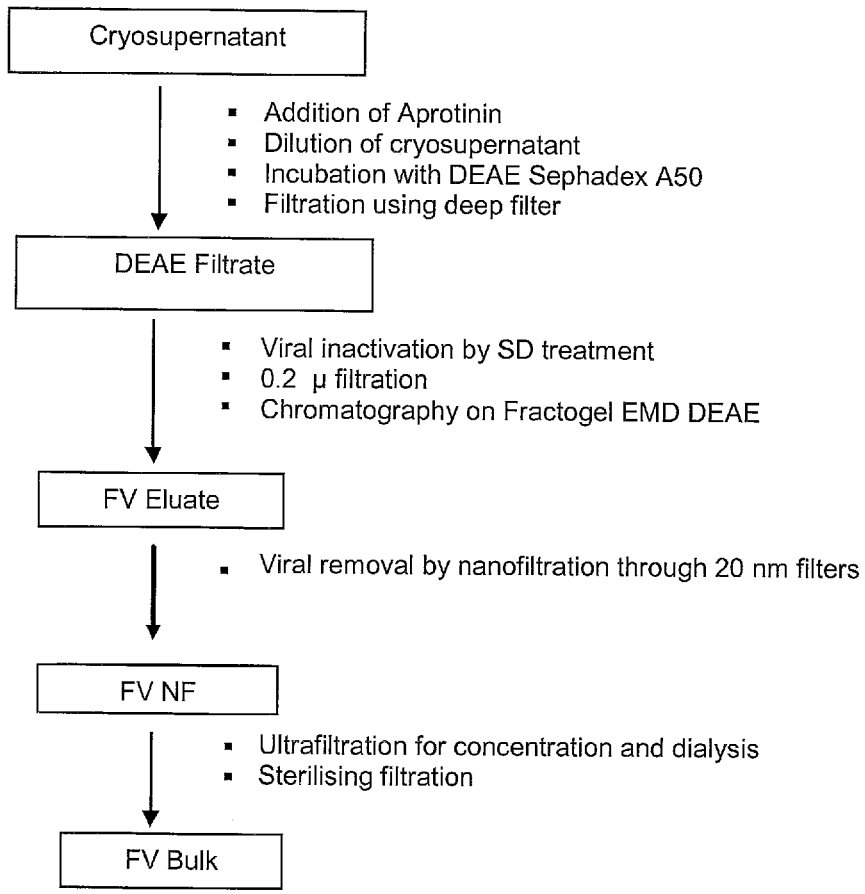
FIG. 1 shows the block outline of one preferred embodiment of the method of the invention, from the raw material to attainment of the FV-containing finished product.

According to the present invention, FV is purified starting from human plasma or from a fractionation intermediate thereof. According to one particular and preferred aspect of the invention, said starting material is cryosupernatant, namely the non-sedimented fraction derived from the plasma cryoprecipitation step, following centrifugation.

Preferably, the cryosupernatant is supplemented with protease inhibitors, used individually or in association thereof, such as, e.g. Aprotinin, Benzamidine, Leupeptin, and STI. For one preferred aspect, Aprotinin is used as the sole protease inhibitor, since it is sufficient to guarantee the integrity of the FV in the end product. The use of aprotinin also has the following advantages: at pH 7.4 it is positively charged and thus does not bind to the anion exchangers, presumably eluting in the unbound fraction in the second chromatography step; subsequently, since it is a small molecule, easily removable by dialysis, it may be later removed in the ultrafiltration step.

The present invention preferably envisages the inclusion of a solvent/detergent treatment, such as Tween 80/TnBP, between the first and second chromatography steps: besides contributing to the viral safety of the product, positioning the viral inactivation step at this level makes it possible to reduce the concentration of both inactivating agents in the FV-containing eluate. Indeed, these tend not to bind to the anion exchange chromatography support subsequently used, and hence the majority is recovered in the non-absorbed fraction, while the FV remains bound to the resin and is eluted by increasing the ionic strength of the equilibration buffer. The use of said inactivating agents included in the aforementioned level of the purification process certainly allows an improvement compared to what is reported in the literature: in the few cases where a viral inactivation step is envisaged, this is performed using heptane, which is then removed by drying, a treatment which is potentially damaging to the integrity of the protein (U.S. Pat. No. 5,219,995).

In addition to the solvent/detergent treatment, a viral removal step has been included downstream of the second chromatography step, involving filtration through 20 nanometer nanofilters. This additional step also protects the product against small non-enveloped viruses, such as for example HAV.

The process described concludes with an ultrafiltration step making it possible to obtain a concentrated and dialysed protein solution, suitable for i.v. administration for the treatment of Parahaemophilia.

According to one preferred aspect of the present invention the cryosupernatant sample is supplemented with Aprotinin at a concentration comprised between 50 and 1100 KIU/ml, and then diluted with WFI to obtain a conductivity value comprised between 3 and 10 mS/Cm, and the pH adjusted to a value comprised between 7.0 and 8.0.

In accordance with the present invention, the sample thus obtained is then incubated in batch mode, at a temperature comprised between 15 and 25° C., with dry or hydrated DEAE Sephadex A50 resin, in a ratio that may vary from 0.15 to 2.0 g of dry resin per liter of diluted sample, for a period of time comprised between 30 and 90 minutes.

According to the present invention, the sample-resin mixture is filtered under vacuum through a Buchner funnel or using disposable capsules, through Pall type K100 pre-filters or the like: the FV is recovered almost entirely in the filtrate, while FII, FVII, FIX and FX are predominantly absorbed on the resin.

The present invention thus envisages the addition of calcium chloride, up to a concentration comprised between 1 and 10 mM, and sodium chloride, up to a concentration comprised between 100 and 130 mM, to the filtered sample, called DEAE filtrate.

According to the present invention, the sample thus treated is subjected to incubation with tween 80 at a concentration comprised between 0.5 and 2%.w/w and tri-n-butyl-phosphate at a concentration comprised between 0.1 and 0.5% w/w at a temperature comprised between 20 and 30° C., for a period of time comprised between 4 and 10 h.

In accordance with the present invention, the solution subjected to viral inactivation treatment is filtered through 0.2 μm cut-off filters, in order to protect the chromatography support subsequently used in the purification process.

In accordance with the present invention, the virally inactivated solution is subjected to column chromatography, preferably on a weak anion exchanger, such as for example: Fractogel EMD-DEAE (Merck), DEAE Toyopearl 650 M (Tosoh), Macro-Prep DEAE (Bio Rad), DEAE Sepharose FF (GE), DEAE Ceramic HyperD F (Pall). According to the present invention, the second chromatography purification step is conducted in binding mode, and is characterised by subsequent increases in the salt concentration allowing the sequential elimination of the proteins not bound to the support during the wash phase, the removal of weakly bound contaminating proteins during the intermediate steps, and selective elution of the FV at higher ionic strength (FV Eluate).

According to the present invention, the second chromatography purification step preferably includes the following steps:
a) conditioning of the weak anion exchanger with aqueous equilibration buffer having a pH comprised between 7.0 and 7.8, containing NaCl at a concentration comprised between 0.05 and 0.13 M, containing calcium chloride at a concentration comprised between 1 and 10 mM, and optionally comprising glycine.
b) loading of the FV enriched fraction;
c) eluting unbound proteins by washing with the equilibration buffer;
d) eluting the weakly bound proteins with an aqueous buffer at a pH comprised between 7.0 and 7.8, containing NaCl at a concentration comprised between 0.14 and 0.17 M, containing calcium chloride at a concentration comprised between 1 and 10 mM, and optionally comprising glycine;
e) eluting a solution containing FV with an aqueous elution buffer at a pH comprised between 7.0 and 7.8, containing NaCl at a concentration comprised between 0.18 and 0.30 M, containing calcium chloride at a concentration comprised between 1 and 10 mM, and optionally comprising glycine.

Said buffer with a pH comprised between 7.0 and 7.8, is obtained for example using citrate, phosphate or Tris.

In accordance with the present invention, the FV-containing eluate is subjected to viral removal by means of a filtration process through 0.1 μm filters (e.g. DJL-Pall) and nanofiltration, performed using 50 and 20 nanometer nanofilters, such as for example DV50 and DV20 (Pall) or N20 (Planova).

According to the present invention, the nanofiltered solution, known as FV NF is subsequently concentrated and dialysed against an appropriate buffer in order to obtain a solution with an FV titre of at least 20 IU/ml, and salt composition compatible with intravenous administration.

In accordance with the present invention, the end product thus obtained, known as FV Bulk, is frozen and stored at −20° C., a condition under which the FV contained in the solution has been shown to be stable.

This method may be used to obtain an FV concentrate suitable for intravenous administration for the treatment of Parahaemophilia or other pathologies associated with FV deficiency.

Besides providing a virally safe purified FV concentrate with high yield, the purification method of the present invention is efficient, reproducible, simple and scalable up to industrial level. The concentrate contains FV at high specific activity, if compared with purification methods using traditional and low cost methods such as ion exchange. The main contaminating proteins that might interfere with the stability of the end product, such as FII, FVII, FVIII, FIX and FX, are present only in trace amounts. Other contaminants such as Fibrinogen, Fibronectin and IgG are below the limit of detection, while, IgA and IgM are present at very low concentrations.

The FV purified using the present method preserves its integrity, as shown by comparison with a plasma standard by means of Western Blot analysis. The invention is further described in the following examples. Said examples are useful for clarifying the invention and do not limit it in any way.

EXPERIMENTAL SECTION

Example 1

Evaluation of FV in Fractionation Intermediates

Figure 2:
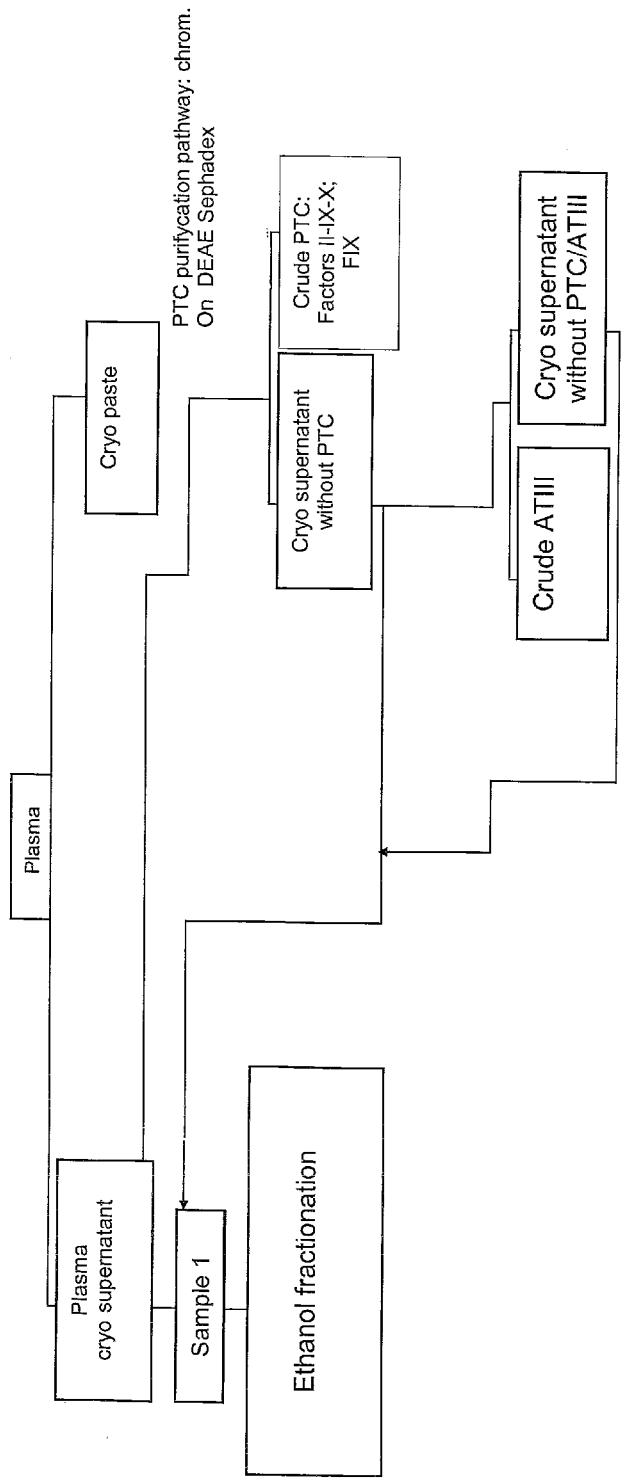
FIG. 2 shows the plasma fractionation outline.

FV activity has been evaluated in the various fractionation intermediates by means of a coagulation test, using commercially available FV deficient plasma (Factor V deficient plasma-IL) and thromboplastin (Recombiplastin2G-IL). The fractionation process examined (FIG. 2) comprises the step of cryoprecipitation and adsorption on weak anion exchange, prior to conventional fractionation steps using ethanol, to obtain albumin and immunoglobulins.

Analysis of the various intermediates has shown the partitioning of almost all the FV into the cryosupernatant (approx. 98%); of this, only 17% of the FV incubated with the DEAE Sephadex A50 anion exchange resin is recovered in the unbound fraction, thus indicating that the majority of the FV binds to the support together with the prothrombin complex components. Indeed, approx. 30% of the FV incubated with the anion exchanger elutes with the PTC, but the protein tends to rapidly lose activity, as demonstrated by analysis of said sample after storage at −20° C. for a few days (Table 1).

TABLE 1

| Intermediate<br>Supernatant without cryo | % FV Step Yield |
|---|---|
| PTC supernatant | 17.09 |
| Fresh crude PTC | 29.58 |
| Crude PTC 7 days at −20° C. | 5.31 |

As precipitation with ethanol proceeds, the recovery of FV tends to reduce, even if not dramatically, and its specific activity (S.A.=IU/mg protein) remains less than that measured in plasma (0.0145 IU/mg).

Example 2

Purification Process a) Preparation of the Starting Material

Supernatant has been used as starting material. The pH of this intermediate has been adjusted to a value of 7.4 using hydrochloric acid, then the sample has been supplemented with Aprotinin up to a concentration of 1000 KIU/ml and diluted approx. 3.36-fold with WFI to give a final conductivity of 4.5 mS/cm.

b) Batch Anion Exchange Chromatography

Non-binding batch chromatography has been performed on DEAE Sephadex A50 anion exchange resin (GE Healthcare). To the cryosupernatant, treated as described in the previous section, has been added the dry DEAE Sephadex A50 resin in a ratio of 0.9 g of dry resin/l of diluted sample, with constant mechanical stirring. Incubation has been conducted at 25° C. for 60 minutes. At the end of incubation, the resin/sample mixture has been filtered through a type K100 depth filter (Pall), trapping the resin and the adsorbed fraction on the filter, while non-adsorbed material is recovered in the filtrate. Under the conditions indicated, it has been possible to separate FV from the prothrombin complex component factors, as reported in table 3:

TABLE 2

| Step | Step % Yield | | | | | |
|---|---|---|---|---|---|---|
| | FV:Act | FVII | FII | FIX | FX | Protein |
| DEAE filtrate | 99.80% | 6.03% | 4.62% | n.d.* | 5.77% | 88.26% |

*results below the detection limit of the test c) Viral in Activation by Solvent/Detergent Mixture The filtered sample has been supplemented with sodium chloride and calcium chloride, such that the solution loaded onto the column in the subsequent chromatography step should have a concentration equal to 5 mM in calcium chloride and 120 mM in sodium chloride. The intermediate thus treated has been subjected to viral inactivation by contact with a mixture of tween 80 (1% w/w) and tri-n-butyl phosphate (0.3% w/w) for 8 h at a controlled temperature of 25±1° C. The sample subjected to viral inactivation has been clarified by filtration through a 0.2 μm cut-off filter as a protection for the subsequent chromatography step.

d) Anion Exchange Column Chromatography

Anion exchange column chromatography has been performed using Fractogel EMD DEAE (Merck) resin packed into a column with a diameter of 5 cm and a height of 17 cm. The column has been equilibrated with 10 mM citrate buffer, containing 120 mM sodium chloride, 5 mM calcium chloride, 120 mM glycine, pH 7.4, at a flow rate of 180 cm/h.

The inactivated and filtered sample has been loaded onto the column as a load of 340 mg of protein/ml of resin, at a flow rate of 130 cm/h. On completion of loading, the column has been washed with 6 volumes of equilibration buffer at a flow rate of 180 cm/h. The proteins bound weakly to the support have then been removed by washing with 6 column volumes of equilibration buffer in which the sodium chloride concentration has been increased to 150 mM. The FV has then been eluted by increasing the sodium chloride concentration in the elution buffer to 200 mM, washing the column with 5 volumes of said buffer at a flow rate of 90 cm/h.

Table 3 reports the characteristics of the solution containing FV eluted from the anion exchange chromatography column:

TABLE 3

| Fraction | FV:Act (IU/ml) | Step % Yield | Protein (mg/ml) | Step % Yield | S.A. (IU/mg) |
|---|---|---|---|---|---|
| Fractogel EMD-DEAE eluate | 3.670 | 100% | 0.207 | 0.13% | 17.729 | e) Nanofiltration

The Fractogel EMD-DEAE eluate has been filtered first of all through a sterilising grade filter and subsequently through a viral grade filter with a porosity of 20 nm. The results obtained from this process are reported in table 4:

TABLE 4

| Step | % FV Step Yield |
|---|---|
| Sterilising filtration | 92.31% |
| 20 nm filtration | 86.34% | f) Concentration/Ultrafiltration

The nanofiltered sample has been subjected to ultrafiltration by means of a device for tangential flow filtration using cassettes with a molecular cut-off of 50 KDa (Pall): the sample has thus been concentrated to a minimum FV titre of 20 IU/ml and dialysed until reaching the desired final formulation. For the dialysis and formulation phases, a buffer containing 10 mM sodium citrate, 110 mM sodium chloride, 120 mM glycine and 1 mM calcium chloride at pH 7.4 has been used. The final solution thus obtained has been subjected to sterilising filtration and filled into vials, then subsequently frozen at −20° C.

The process described in the present example thus makes it possible to obtain an FV concentrate with high yields and a good purification index (PI) compared to the starting material, as reported in table 5:

TABLE 5

| Fraction | % FV Process Yield | S.A. (IU/mg) | P.I |
|---|---|---|---|
| Bulk FV | 73.4% | 20.33 | 782 |

Example 3

Finished Product Characterisation

This example reports a table (Table 6) summarising the main characteristics of the product obtained from application of the protocol described in example 2.

TABLE 6

| | |
|---|---|
| IgG (mg/ml) | n.d.* |
| FIB (mg/ml) | n.d.* |
| FNC (mg/ml) | n.d.* |
| IgM (mg/l) | 0.084 |
| IgA (mg/l) | 0.007 |
| FV:Act (IU/ml) | 24.91 |
| FII (IU/ml) | 0.01 |
| FX (IU/ml) | 0.03 |
| FIX (IU/ml) | 0.04 |
| FVII (IU/ml) | 0.04 |

TABLE 6-continued

| Protein C (IU/ml) | n.d.* |
|---|---|
| Protein (mg/ml) | 1.23 |

*results below the detection limit of the test

Figure 3:
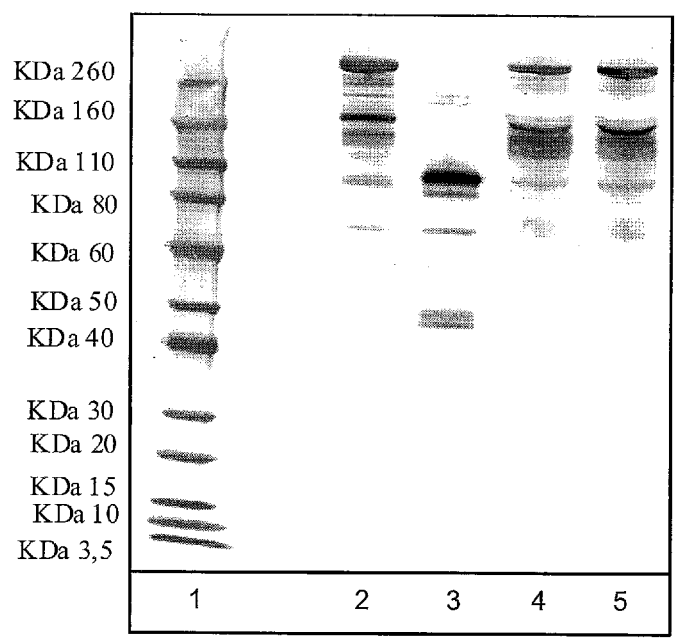
FIG. 3 shows the Western blot analysis performed on finished product compared with reference standards in order to verify the integrity of the FV. 1.MW Standard, 2.Standard FV, 3.Standard FVa, 4.FV Bulk 01; 5.FV Bulk 02.

In the finished product obtained, the integrity of the protein of interest has also been assessed by western blotting using antibody directed against the FV heavy chain. The results of this test are reported in FIG. 3. Integrity and the absence of FV activation in the final bulk are also shown by assaying for activated factors: this test, which detects the presence of coagulation cascade activation phenomena, has also given a negative result.

The invention claimed is:

1. Process for the purification of FV starting from human plasma or an FV-enriched intermediate fraction, wherein the protein is intact; said process comprising two chromatography steps on weak anion exchangers, wherein the first step is conducted in FV "non-binding" mode while the second step is in FV "capture" mode;
   wherein the two chromatography steps are separated by at least one viral inactivation step performed by solvent-detergent treatment;
   wherein after the second chromatography step, the FV containing solution is subjected to a viral removal step by nanofiltration;
   wherein cryosupernatant is used as starting material;
   wherein cryosupernatant is diluted with WFI to obtain a conductivity value comprised between 3 and 10 mS/Cm and supplemented with protease inhibitor Aprotinin and contacted with the first weak anion exchanger resin in a ratio that may vary from 0.15 to 2.0 g of dry resin per liter of diluted cryosupernatant.

2. The process according to claim 1, wherein both weak anion exchangers of the two chromatography steps belong to the category of weak exchangers characterised by the diethylaminoethyl (DEAE) functional group.

3. The process according to claim 1, wherein the cryosupernatant sample is supplemented with Aprotinin at a concentration comprised between 50 and 1100 KIU/ml, and then diluted with WFI to obtain a conductivity value comprised between 3 and 10 mS/Cm, and the pH adjusted to a value comprised between 7.0 and 8.0.

4. The process according to claim 1, wherein the weak anion exchange matrix used in the first step is of Sephadex type, i.e. dextran-based.

5. The process according to claim 4, wherein the first chromatography step is conducted in batch mode, at a temperature comprised between 15 and 25° C., using dry or hydrated DEAE Sephadex A50 resin, in a ratio of 0.9 g of dry resin per liter of diluted sample, for a period of time comprised of between 30 to 90 minutes.

6. The process according to claim 1 wherein the weak anion exchanger used in the second step consists of a "tentacle" structured, synthetic, hydrophilic support containing long polymeric chains, to the ends of which are bonded DEAE groups.

7. The process according to claim 6, wherein the second chromatography step comprises the following steps:
   a) conditioning of the weak ion exchange resin with aqueous equilibration buffer having a pH comprised between 7.0 and 7.8, containing NaCl at a concentration comprised between 0.05 and 0.13 M, containing calcium chloride at a concentration comprised between 1 and 10 mM, and optionally comprising glycine;
   b) loading of the fraction enriched in the proteins of interest;
   c) eluting unbound proteins by washing with equilibration buffer;
   d) eluting the weakly bound proteins with an aqueous buffer at a pH comprised between 7.0 and 7.8, containing NaCl at a concentration comprised between 0.14 and 0.17 M, containing calcium chloride at a concentration comprised between 1 and 10 mM, and optionally comprising glycine;
   e) eluting a solution containing FV with an elution buffer at a pH comprised between 7.0 and 7.8, containing NaCl at a concentration comprised between 0.18 and 0.30 M, containing calcium chloride at a concentration comprised between 1 and 10 mM, and optionally comprising glycine.

* * * * *